United States Patent [19]

Percival et al.

[11] 4,340,862
[45] Jul. 20, 1982

[54] IMAGING SYSTEMS

[75] Inventors: William S. Percival, London; Peter E. Walters, Southall, both of England

[73] Assignee: Picker International Limited, Wembley, England

[21] Appl. No.: 102,113

[22] Filed: Dec. 10, 1979

[30] Foreign Application Priority Data

Dec. 13, 1978 [GB] United Kingdom ............... 48214/78

[51] Int. Cl.³ ............................................ G01N 27/00
[52] U.S. Cl. .................................... 324/309; 324/312
[58] Field of Search ....................... 324/300, 309, 312; 250/336, 362

[56] References Cited
U.S. PATENT DOCUMENTS 3,778,614 12/1973 Hounsfield ........................... 250/362
3,924,129 12/1975 Gordon ................................ 250/336
4,070,611 1/1978 Ernst ................................... 324/312

Primary Examiner—Michael J. Tokar
Attorney, Agent, or Firm—Fleit & Jacobson

[57] ABSTRACT

In an NMR examining arrangement for producing an image of a region, generally a planar slice, of a body, it has been suggested to derive, from the resonance signals, a plurality of values, for strips in the slice, and then to convolve them with a convolution function to be suitable for back projection in the manner known for x-ray signals. In this invention it is proposed to modulate the resonance signals with a suitable function and then to Fourier transform them but not to convolve them. The modulation function is chosen to give after Fourier transformation the same effect as the convolution would have given. It is suggested that the modulation function should be the inverse Fourier Transform of the desired convolution function.

10 Claims, 6 Drawing Figures

IMAGING SYSTEMS

The present invention relates to systems for providing images of distributions of a quantity, in a chosen region of a body, by gyromagnetic resonance, particularly nuclear magnetic resonance.

It has been proposed that nuclear magnetic resonance be used to provide distributions of water protons or similar molecules or relaxation time constants in sectional slices of bodies and that this is particularly useful for medical examination of patients.

In a preferred method it has been suggested that the NMR data can be analysed by techniques similar to those known for distributions of X-ray attenuation provided by computerised tomography systems. In our copending U.S. Pat. applications Ser. Nos. 041,424, 039,650, 040,289, 039,649 and 048,777 there has been described and claimed such a method and an apparatus for operating it. That method requires the excitement of different parts of the body at different resonance frequencies and the sensing, at appropriate frequencies, of resonance signals each of which relates only to one part.

A basic steady magnetic field $H_{zo}$ is applied to the body in one direction which is defined as the z-direction. This direction is generally arranged to be parallel to the long axis of the body. A further $H_z$ field, $G_z$ is applied to have a gradient in the z-direction so that $G_z = \partial H_z/\partial z$. This provides a unique total field value in a chosen cross-sectional slice of the patient. A rotating RF field, $H_1$, is applied at a frequency chosen to excite resonance in the selected slice. The result is that the molecules of the body resonate but only in that slice. The resonance signal from the slice can then be detected. However, as it is detected there is applied a further field $G_r = \partial H_z/\partial r$ which is in the z-direction but has a gradient in a direction r perpendicular to z. This causes frequency dispersion of the resonant frequencies in the r-direction and consequent frequency dispersion of the resonance signal detected.

This invention is not concerned with the derivation of this resonance signal or with the apparatus by which it is obtained. The invention is, however, concerned with the derivation of data for the slice from the resonance signal.

The signal covers a range of frequencies and the amplitude at a frequency range f to $f = \delta f$ is a resonance signal for a strip in the slice perpendicular to r and extending from r to $r + \delta r$. Thus if the signal is frequency analysed a plurality of signals are provided each for a different one of a plurality of parallel strips, each of width $\delta r$, perpendicular to r. Frequency analysis can be achieved by using a plurality of phase sensitive detectors. It is, however, preferred to achieve this by Fourier transformation of the total signal. In practice the total signal is applied to two phase sensitive detectors with their oscillators at the same frequency, $f_o$, but whose phases differ by 90°. This provides sine and cosine terms of the total resonance signal. The two terms are then applied to known Fourier transform circuits. Such a procedure is usually required because the frequencies are, in general, referenced to a centre frequency for a line central to the slice and allows differentiation between identical positive and negative frequencies for lines equispaced from the reference. That is, one line is given by the sum of sine and cosine and the opposing line by the difference. The Fourier transformation yields total signals for excited nuceli in each of a plurality of parallel strips in the slice. These signals can be called 'edge readings' and are analoguous to the edge readings in X-ray (CT) scanning which are total X-ray attentuation for beam paths, often parallel, in a slice of the patient.

As in the X-ray procedure, further sets of edge readings are obtained for sets of strips in the slice, each set being at a different orientation.

A suitable procedure for processing such data is described and claimed in U.S. Pat. No. 3,924,129. The procedure involves convolving each set of edge readings with a suitable convolution function and summing all of the convolved sets as a layergram, as explained in said patents.

The procedure and equipment for carrying out this convolution procedure are now well known. However it is a relatively lengthy procedure which in the NMR case must be carried out following a Fourier transform procedure. It is an object of this invention to provide an alternative arrangement.

According to the invention there is provided a circuit for processing a nuclear magnetic resonance signal to provide an output signal which is substantially the convolution of the Fourier transform of the resonance signal, with a predetermined convolution function, the circuit including function generating means providing a modulating function, means for modulating the resonance signal with said modulating function and means for Fourier transforming the modulated signal to provide the output signal.

Preferably the modulating function is the inverse Fourier transform of the convolution function.

In order that the invention may be clearly understood and readily carried into effect it will now be described by way of example with reference to the accompanying drawings, of which:

Figure 1:
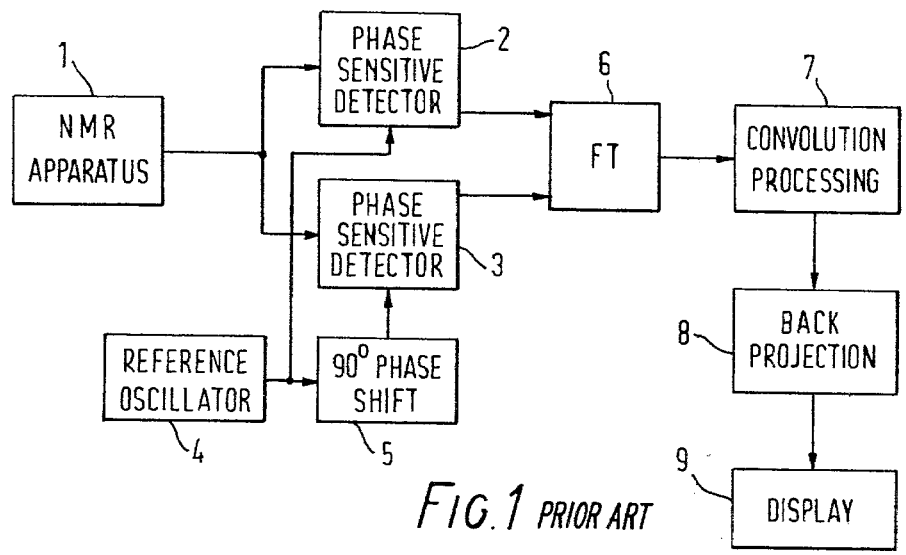
FIG. 1 shows a prior circuit for processing NMR signals.

The prior arrangement for processing NMR signals is shown in its preferred form in FIG. 1. The NMR apparatus is indicated generally at 1 and is of suitable known form, perhaps as described in the said co-pending applications. The total signals are applied to two phase sensitive detectors 2 and 3, both of which receive reference oscillations from an oscillator 4, the reference to detector 33 being subject to a 90° phase shift in a unit 5. Thus detectors 2 and 3 provide sine and cosine components to a Fourier transform circuit 6, of well known type, which then provides a frequency spectrum for the signal. This spectrum is a sequence of signals which are the required edge readings. They are then provided to a processing unit 7 which applies convolution processing such as described in the said United States Patents. The processed edge readings are then back projected in a unit 8 and the resulting picture can be stored or displayed in a suitable display 9. The back projection and display are identical to the procedure now well known for X-ray processing and described in U.S. Pat. No. 3,778,614.

It is now proposed to improve the processing shown in FIG. 1 by modifying the signals prior to Fourier transform circuits 6 so that the output of 6 does not require convolution processing but can be directly back projected to give the final picture. This is achieved by multiplying the time varying NMR signal f(t), prior to Fourier transform, by a suitably derived function a(t). The function a(t) f(t) is conveniently formed by first sampling the time varying signal at appropriate intervals, of not more than half a cycle of the highest frequency, giving $f(t_r)$ for the r'th sample. This is then multiplied by a $(t_r)$ at time $t_r$ for all r. The resultant signal is then Fourier transformed in the usual way.

Figure 2:
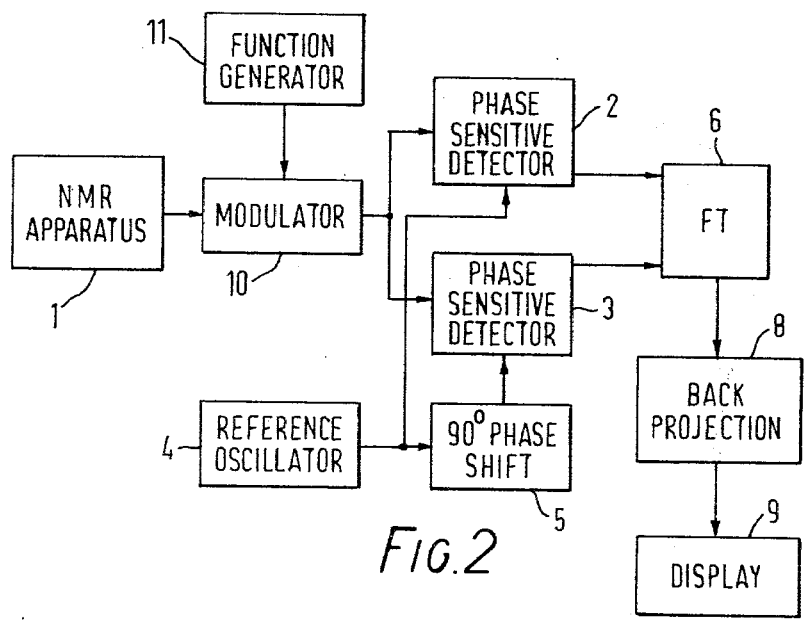
FIG. 2 shows a modification of the circuit of FIG. 1 to implement this invention.

One embodiment of this invention is shown in the block diagrammatic circuit of FIG. 2. This differs from the prior circuit of FIG. 1 in two respects. The first difference is that the NMR signal as derived at 1 is multiplied in a modulator 10 by the function a(t) which is created in a function generator 11. This modulator can be of the normal type used in broadcast radio transmitters but should be capable of handling 100% modulation without significant distortion. The second difference is consequential on the multiplication by a(t) and is that the convolution circuits 7 are not included. The input to 8 is substantially the same as in FIG. 1 if the function a(t) is properly chosen.

To achieve the correct result in FIG. 2 the function a(t) is chosen to be the inverse Fourier transform of the convolution function which would have been applied at circuits 7.

Figure 3:
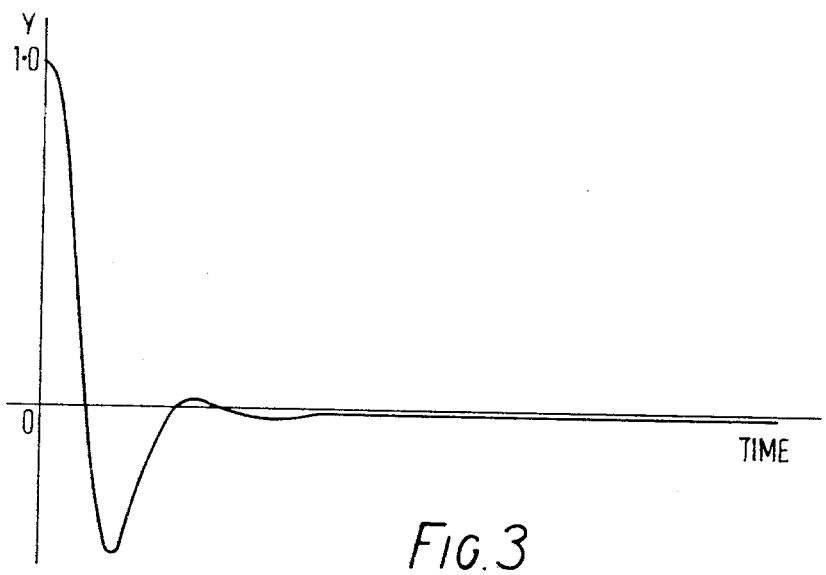
FIG. 3 shows part of a convolution function known for X-ray processing.

In the said U.S. Pat. No. 3,924,129 there has been proposed a symmetrical convolution function of which the first eleven terms and every fifth term thereafter, to one side of the centre zero term are as shown in Table 1. The same half of the function is shown in FIG. 3. This function is expressly created for X-ray CT analysis but may be used for NMR.

It is now proposed, that the improved processing may be implemented, to the same effect as use of that convolution function, it a(t) is as shown, also for one side of the centre zero, in Table 2. This function is shown for one half in FIG. 4.

Figure 4:
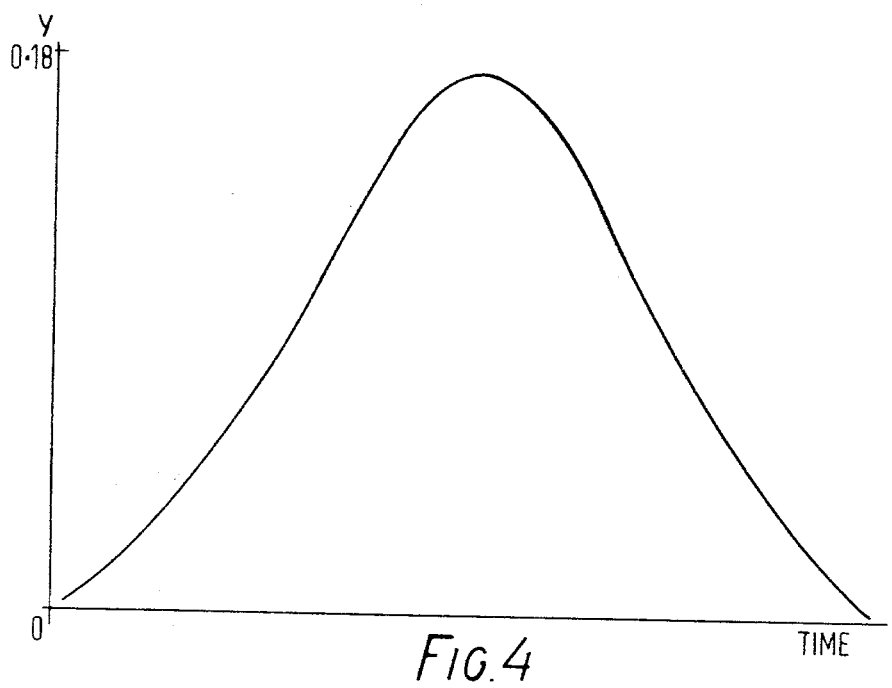
FIG. 4 is the inverse Fourier transform of the complete function of FIG. 3.

It should be noted that FIGS. 3 and 4 are not to scale, being merely illustrative of the form of function involved. The required function should be obtained by inverse Fourier transformation of the desired convolution function.

Figure 5:
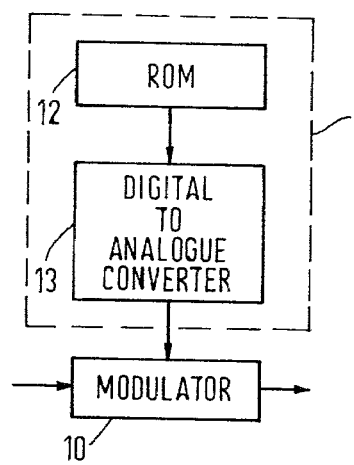
FIG. 5 shows one embodiment of the function generator of FIG. 2.

It will be apparent that a function generator to provide the desired signal a(t) may readily be provided as shown in FIG. 5, by storing, in a ROM store 12, values of amplitude at different times of the desired function. These may be used to control a plurality of oscillators, but is preferable to feed the stored numbers to a standard digital to analogue converter 13. Such a converter may be arranged to multiply by the reference voltage and thus effectively to be the modulator 10 as well. The function generator may take other forms as desired.

Figure 6:
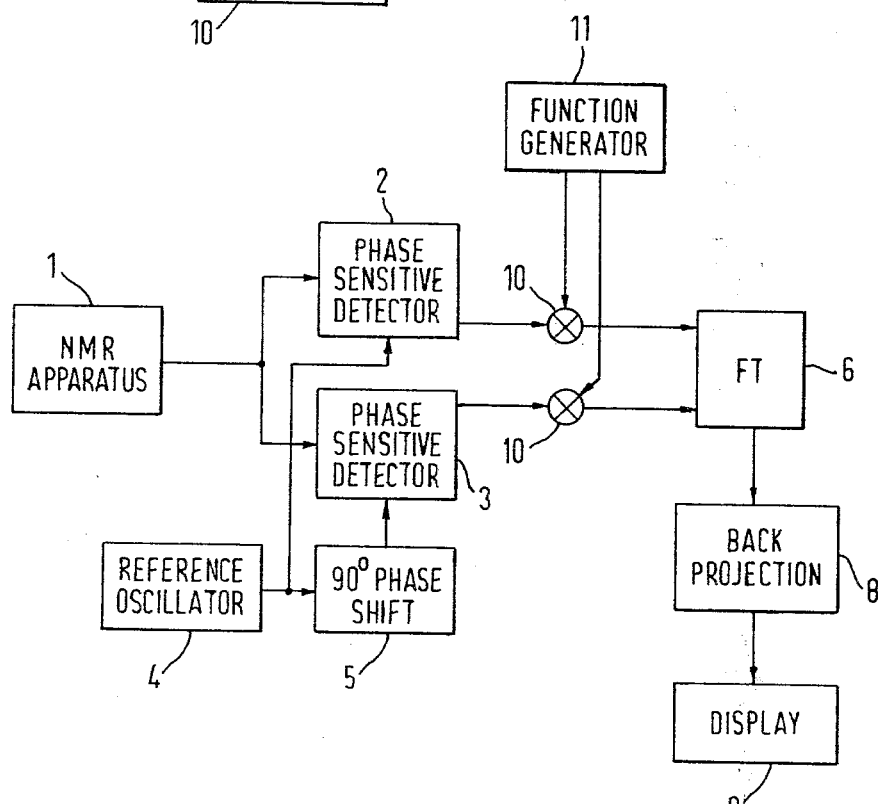
FIG. 6 is a further modification of the circuit of FIG. 2.

Although the circuit of FIG. 2 is arranged to multiply the NMR signal by a(t) prior to detectors 2 and 3, it is now proposed in a preferred embodiment of this invention that the function may be applied after detection provided that it is still applied prior to Fourier transform. An adaptation of FIG. 2 to achieve this effect is shown in FIG. 6. In that circuit modulator 10 is provided in the output of each of detectors 2 and 3, both multiplying by the same signal from function generator.

It has been found that if modulation is applied at this stage the same function is required as required in FIG. 2. Thus no change is required to the construction of generator 11. The only change is to its disposition.

TABLE 1

| Term | Amplitude |
|---|---|
| 0 | 1.000000 |
| 1 | −0.444516 |
| 2 | 0.015011 |
| 3 | −0.025484 |
| 4 | −0.008697 |
| 5 | −0.006651 |
| 6 | −0.004478 |
| 7 | −0.003330 |
| 8 | −0.002552 |
| 9 | −0.002020 |
| 10 | −0.001638 |
| 15 | −0.000730 |
| 20 | −0.000411 |
| 25 | −0.000263 |
| 30 | −0.000183 |
| 35 | −0.000136 |
| 40 | −0.000106 |
| 45 | −0.000078 |
| 50 | −0.000071 |
| 55 | −0.000062 |
| 60 | −0.000047 |
| 64 | −0.000039 |

TABLE 2

| Term | Amplitude |
|---|---|
| 1 | 0.00068 |
| 5 | 0.00897 |
| 10 | 0.02049 |
| 15 | 0.03252 |
| 20 | 0.04545 |
| 25 | 0.05952 |
| 30 | 0.07486 |
| 35 | 0.09157 |
| 40 | 0.10933 |
| 45 | 0.12755 |
| 50 | 0.14498 |
| 55 | 0.15968 |
| 60 | 0.16975 |
| 65 | 0.17332 |
| 70 | 0.16975 |
| 75 | 0.15968 |
| 80 | 0.14498 |
| 85 | 0.12755 |
| 90 | 0.10933 |
| 95 | 0.09157 |
| 100 | 0.07486 |
| 105 | 0.05952 |
| 110 | 0.04545 |
| 115 | 0.03252 |
| 120 | 0.02049 |
| 125 | 0.00897 |
| 128 | 0.00219 |

It has been assumed hereinbefore that the time varying signal f(t) is the inverse Fourier transform of the frequency spectrum of the excited nuclei. In fact the measured f(t) starts at full excitation and decays to zero. The full signal for transform is conventionally obtained from that measured by reflection at the zero axis and the same process is carried out for this invention. The full signal can also be obtained by known spin-echo techniques.

It should be understood that instead of using a(t) it is possible, although less efficient, to pass the time varying signal f(t) through a suitable electrical filter network.

Other variations of the invention will be apparent to those with the appropriate skills.

Furthermore although the invention has been described in terms of NMR applied to a planar slice of a body, it is applicable to similar procedures for examining volumes of the body.

Although the invention has been described in terms of NMR signals representing parallel strips it will be understood that this is not a limitation imposed by the processing, which is, with an appropriate choice of convolution function, applicable to strips inclined to each other. It is essentially a practical consideration since it is extremely convenient for the NMR apparatus to provide the data in such a parallel form.

I claim:

1. A circuit for processing a nuclear magnetic resonance signal to provide an output signal which is substantially the convolution of the Fourier transform of the resonance signal, with a predetermined convolution function, the circuit including function generating means providing a modulation function which is substantially the inverse Fourier Transform of the predetermined convolution function, means for modulating the resonance signal with said modulating function and means for Fourier transforming the modulated signal to provide the output signal.

2. A circuit according to claim 1 including phase sensitive detectors receiving said resonance signal to provide sine and cosine components thereof for Fourier Transformation and wherein the modulating means is disposed to modulate said resonance signal by said function prior to said detectors.

3. A circuit according to claim 1 including phase sensitive detectors receiving said resonance signal to provide sine and cosine components thereof for Fourier Transformation and wherein the modulating means comprises modulators disposed to modulate the sine and cosine components by said function prior to Fourier Transformation.

4. A circuit according to claim 1 in which the function generating means includes a store holding values of amplitude at different frequencies of the desired function and means for providing the function in response thereto.

5. A circuit according to claim 4 in which the means for providing the function is a digital to analogue converter.

6. A circuit according to claim 5 in which said converter also forms said modulating means.

7. A nuclear magnetic resonance arrangement for examination of a body, the arrangement including a nuclear magnetic resonance examining apparatus producing resonance signals for resonance dispersed in a plurality of different directions in a region of the body, a processing circuit according to any one of claims 1, 2, 3, 4, 5 or 6 for processing the signals into signals for a plurality of sets of linear strips in the region, means for back-projecting the processed signals to provide a representation of said region and means for displaying said representation.

8. A method of processing nuclear magnetic resonance signals originating from a plurality of sets of parallel linear strips in a region of a body each resonance signal resulting from dispersion of resonance, in the region, in a different direction and the strips of a set being perpendicular to the respective direction to provide groups of output signals each group being the convolution of the resonance signal for one direction of dispersion with a predetermined convolution function, the convolution being effectively achieved by modulating the resonance signal with the inverse Fourier transform of the convolution function and Fourier transforming the modulated signal.

9. A method according to claim 8 in which sine and cosine components of the resonance signal are formed prior to Fourier Transformation and the modulation is applied to said components.

10. A method of examining a body by nuclear magnetic resonance including exciting resonance in a region of the body, dispersing the resonance in a plurality of different directions, processing the resonance signal by the method according to claim 8 or claim 9 to form signals for a plurality of sets of linear strips in said region and back projecting the processed signals onto a matrix of elements notionally defined in said region, to form a representation of said region.

* * * * *